US00PP19713P2

(12) United States Plant Patent
Sakazaki

(10) Patent No.: US PP19,713 P2
(45) Date of Patent: Feb. 17, 2009

(54) ***CALIBRACHOA* PLANT NAMED 'USCALI413-11'**

(50) Latin Name: ***Calibrachoa* sp.**
Varietal Denomination: USCALI413-11

(75) Inventor: Ushio Sakazaki, Shiga (JP)

(73) Assignee: Plant 21 LLC, San Marco, CA (US)

( * ) Notice: Subject to any disclaimer, the term of this patent is extended or adjusted under 35 U.S.C. 154(b) by 0 days.

(21) Appl. No.: 12/069,035

(22) Filed: Feb. 6, 2008

(51) Int. Cl.
*A01H 5/00* (2006.01)

(52) U.S. Cl. ..... Plt./413
(58) Field of Classification Search ..... Plt./413
See application file for complete search history.

*Primary Examiner*—Kent L Bell
(74) *Attorney, Agent, or Firm*—C. A. Whealy

(57) ABSTRACT

A new and distinct cultivar of *Calibrachoa* plant named 'USCALI413-11', characterized by its compact, mounding and outwardly spreading to trailing growth habit; numerous orange-colored flowers with red-colored centers and venation; and good garden performance.

1 Drawing Sheet

Botanical designation: *Calibrachoa sp.*
Cultivar denomination: 'USCALI413-11'.

BACKGROUND OF THE INVENTION

The present invention relates to a new and distinct cultivar of *Calibrachoa,* botanically known as *Calibrachoa sp.* and hereinafter referred to by the name 'USCALI413-11'.

The new *Calibrachoa* is a product of a planned breeding program conducted by the Inventor in Hikone, Shiga, Japan. The objective of the breeding program is to create new *Calibrachoa* cultivars with uniform plant habit and attractive flowers.

The new *Calibrachoa* originated from a cross-pollination made by the Inventor on Apr. 17, 2004 in Hikone, Shiga, Japan of a proprietary seedling selection of *Calibrachoa sp.* identified as code number CJ04-23, not patented, as the female, or seed, parent with a proprietary seedling selection of *Calibrachoa sp.* identified as code number CJ04-22, not patented, as the male, or pollen, parent. The new *Calibrachoa* was discovered and selected by the Inventor as a single flowering plant within the progeny of the stated cross-pollination in a controlled environment in Gensingen, Germany on May 24, 2005.

Asexual reproduction of the new *Calibrachoa* by terminal cuttings in a controlled environment in a greenhouse in Gensingen, Germany since May 25, 2005 has shown that the unique features of this new *Calibrachoa* are stable and reproduced true to type in successive generations.

SUMMARY OF THE INVENTION

The cultivar USCALI413-11 has not been observed under all possible environmental conditions. The phenotype may vary somewhat with variations in environment and cultural practices such as temperature, daylength and light intensity without, however, any variance in genotype.

The following traits have been repeatedly observed and are determined to be the unique characteristics of 'USCALI413-11'. These characteristics in combination distinguish 'USCALI413-11' as a new and distinct cultivar of *Calibrachoa:*

1. Compact, mounding and outwardly spreading to trailing growth habit.
2. Numerous orange-colored flowers with red-colored centers and venation.
3. Good garden performance.

The new *Calibrachoa* can be compared to plants of the female parent selection. Plants of the new *Calibrachoa* differ from plants of the female parent selection in the following characteristics:

1. Plants of the new *Calibrachoa* are not as upright as plants of the female parent selection.
2. Plants of the new *Calibrachoa* and the female parent selection differ in flower color as plants of the female parent selection have apricot orange-colored flowers.

Plants of the new *Calibrachoa* can be compared to plants of the male parent selection. Plants of the new *Calibrachoa* differ from plants of the male parent selection in the following characteristics:

1. Plants of the new *Calibrachoa* are more upright than plants of the male parent selection.
2. Plants of the new *Calibrachoa* and the male parent selection differ in flower color as plants of the male parent selection have yellow-colored flowers.

Plants of the new *Calibrachoa* can be compared to plants of the cultivar Sunbelfire, disclosed in U.S. Plant Pat. No. 16,684. In side-by-side comparisons conducted in Gensingen, Germany, plants of the new *Calibracho* differed from plants of the cultivar Sunbelfire in the following characteristics:

1. Plants of the new *Calibrachoa* flowered earlier than plants of the cultivar Sunbelfire.
2. Plants of the new *Calibrachoa* had larger flowers than plants of the cultivar Sunbelfire.
3. Plants of the new *Calibrachoa* and the cultivar Sunbelfire differed in flower color as plants of the cultivar Sunbelfire did not have red-colored centers.

BRIEF DESCRIPTION OF THE PHOTOGRAPHS

The accompanying colored photographs illustrate the overall appearance of the new *Calibrachoa*, showing the colors as true as it is reasonably possible to obtain in colored reproductions of this type. Colors in the photographs may differ slightly from the color values cited in the detailed botanical description which accurately describe the colors of the new *Calibrachoa*.

The photograph at the bottom of the sheet comprises a side perspective view of a typical flowering plant of 'USCALI413-11' grown in a container.

The photograph at the top of the sheet comprises a close-up of typical flowers and leaves of 'USCALI413-11'.

DETAILED BOTANICAL DESCRIPTION

The aforementioned photographs and following observations, measurements and values describe plants grown in Bonsall, Calif., under commercial practice during the autumn in an outdoor nursery with day temperatures ranging from 7° C. to 35° C. and night temperatures ranging from 7° C. to 21° C. Rooted young plants were grown for about nine weeks in one-gallon containers. In the following description, color references are made to The Royal Horticultural Society Colour Chart, 1995 Edition, except where general terms of ordinary dictionary significance are used.

Botanical classification: *Calibrachoa sp.* cultivar USCALI413-11.

Parentage:

*Female, or seed, parent.*—Proprietary seedling selection of *Calibrachoa sp.* identified as code number CJ04-23, not patented.

*Male, or pollen, parent.*—Proprietary seedling selection of *Calibrachoa sp.* identified as code number CJ04-22, not patented.

Propagation:

*Type.*—By terminal cuttings.

*Time to produce a rooted young plant, summer.*—About three weeks at temperatures of 20° C.

*Time to produce a rooted young plant, winter.*—About four weeks at temperatures of 20° C.

*Root description.*—Fine; white in color.

*Rooting habit.*—Freely branching; dense.

Plant description:

*Plant and growth habit.*—Compact, mounding and outwardly spreading to trailing plant habit. Freely branching habit with about eight primary lateral branches each with multiple secondary lateral branches; pinching enhances branching. Moderately vigorous growth habit.

*Plant height.*—About 16 cm.

*Plant diameter.*—About 55.5 cm.

Lateral branch description:

*Length.*—About 34 cm.

*Diameter.*—About 3 mm.

*Internode length.*—About 2.1 cm.

*Strength.*—Strong.

*Aspect.*—Initially upright to outwardly spreading to trailing.

*Texture.*—Pubescent.

*Color.*—146B.

Foliage description:

*Arrangement.*—Before flowering, alternate, simple; after flowering, opposite, simple.

*Length.*—About 3 cm.

*Width.*—About 1.3 cm.

*Shape.*—Elliptical.

*Apex.*—Broadly acute to rounded.

*Base.*—Attenuate.

*Margin.*—Entire.

*Texture, upper and lower surfaces.*—Pubescent.

*Venation pattern.*—Pinnate; arcuate.

*Color.*—Developing foliage, upper and lower surfaces: 146A. Fully expanded foliage, upper and lower surfaces: 146B; venation, 146C to 146D.

*Petiole.*—Length: About 7 mm. Diameter: About 2 mm. Texture, upper and lower surfaces: Pubescent. Color, upper surface: 146C. Color, lower surface: 146D.

Flower description:

*Flower arrangement and habit.*—Single salverform flowers arranged singly arising from leaf axils. Freely flowering habit with usually about 26 open flowers and flower buds per lateral branch. Flowers persistent. Flowers face upright to mostly outwardly.

*Fragrance.*—None detected.

*Natural flowering season.*—Plants of the new *Calibrachoa* initiate and develop flowers about four to six weeks after planting. Plants flower continuously from April to September in Southern California.

*Flower longevity.*—Individual flowers last about one week on the plant.

*Flower diameter.*—About 2.5 cm by 2.6 cm.

*Flower length (height).*—About 2.8 cm.

*Flower throat diameter.*—About 5 mm by 7 mm.

*Flower tube diameter, base.*—About 2.5 mm.

*Flower tube length.*—About 1.8 cm.

*Flower bud.*—Shape: Elongated oblong, narrow. Length: About 2.3 cm. Diameter: About 5 mm. Color: 164B.

*Corolla.*—Arrangement: Five petals fused at the base and opening into a flared trumpet. Petal length from throat: About 1.1 cm. Petal lobe width: About 1.3 cm. Petal shape: Roughly spatulate. Petal apex: Obtuse, slightly mucronate. Petal margin: Entire. Petal texture, upper surface: Smooth, satiny. Petal texture, lower surface: Pubescent. Throat texture: Smooth, satiny. Tube texture: Pubescent. Color: Petal, when opening, upper surface: 168C. Petal, when opening, lower surface: 164B. Petal, fully opened, upper surface: 168C; color becoming closer to 167C with development; towards the throat, more dull than 46A; venation, 46B. Petal, fully opened, lower surface: 24C tinted with 181B; venation, 46A. Throat: 5A; venation, 185A. Tube: 14D; venation, 185A.

*Calyx.*—Arrangement: One star-shaped calyx tube with five sepals fused at the base. Sepal length: About 1.2 cm. Sepal width: About 2.5 mm. Sepal shape: Lanceolate. Sepal apex: Acute. Sepal margin: Entire. Sepal texture, upper and lower surfaces: Pubescent. Color, upper surface: 137B. Color, lower surface: 137C.

*Peduncles.*—Length: About 2.1 cm. Diameter: About 1 mm. Angle: About 30° to 45° from stem axis. Strength: Moderately strong. Texture: Pubescent. Color: 147B.

*Reproductive organs.*—Stamens: Quantity/arrangement: About five per flower. Anther shape: Oval. Anther length: About 1 mm. Anther color: 10A. Pollen amount: Sparse. Pollen color: 10A. Pistils: Quantity: One per flower. Pistil length: About 1.3 cm. Style length: About 1 cm. Style color: 145C. Stigma shape: Rounded. Stigma color: 145A. Ovary color: 145A. Seed/fruit: Seed and fruit development have not been observed on plants of the new *Calibrachoa*.

Garden performance: Plants of the new *Calibrachoa* have been observed to have good garden performance and tolerate wind, rain and temperatures ranging from about 1° C. to about 40° C.

Pathogen/pest resistance: Plants of the new *Calibrachoa* have been observed to be somewhat resistant to *Thielaviopsis*. Plants of the new *Calibrachoa* have not been observed to be resistant to pests and other pathogens common to *Calibrachoa*.

It is claimed:

1. A new and distinct *Calibrachoa* plant named 'USCALI413-11' as illustrated and described.

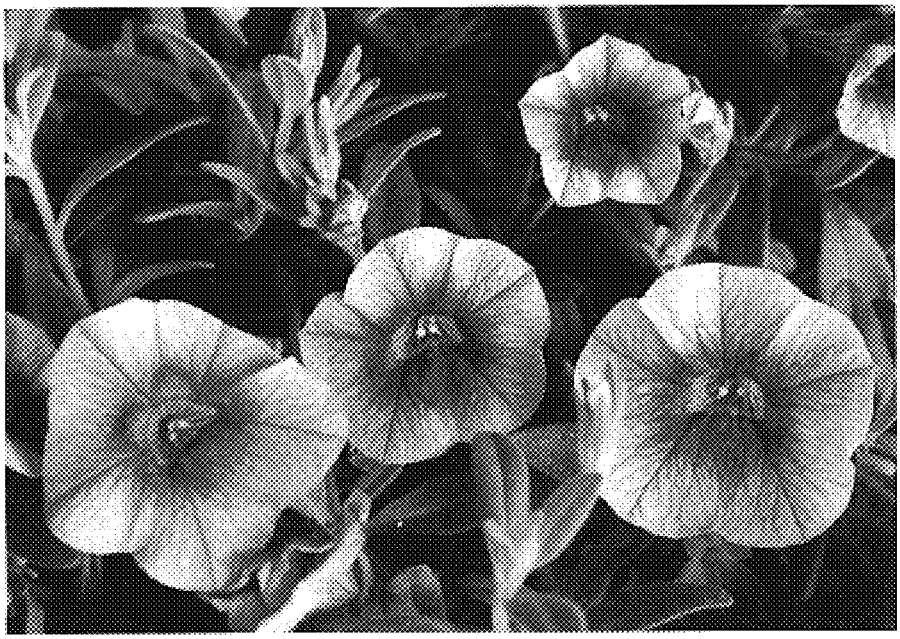
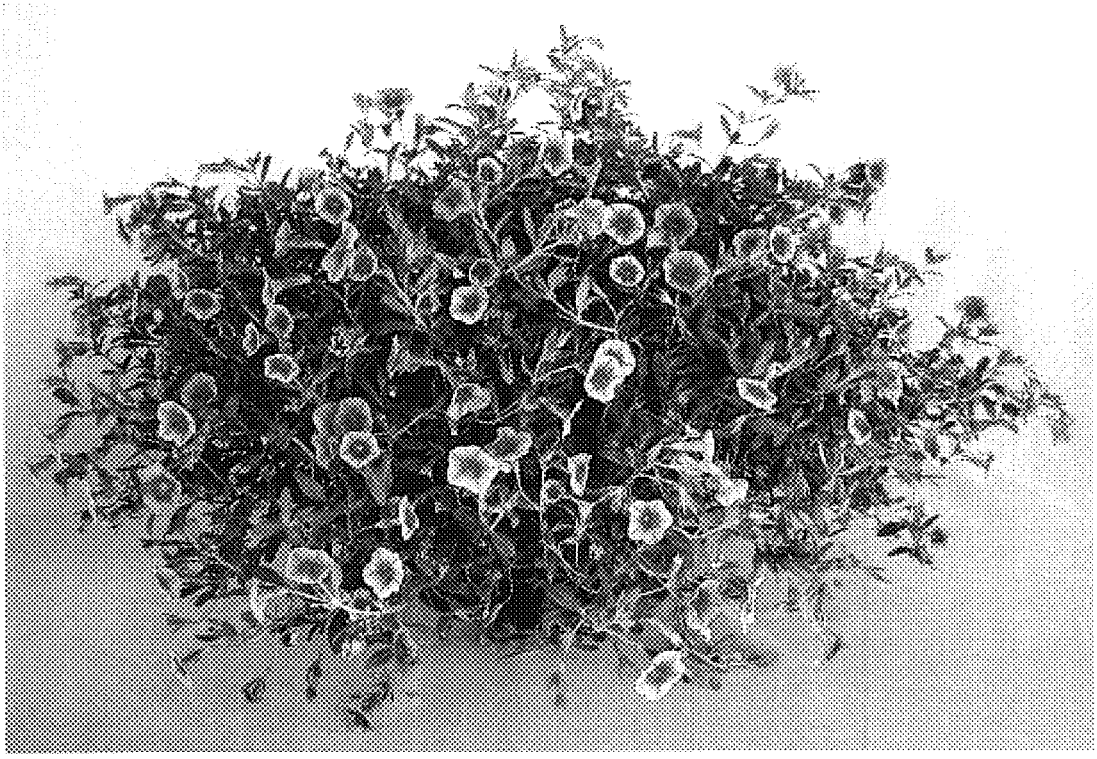

* * * * *